United States Patent [19]

Tensmeyer

[11] 4,042,325

[45] Aug. 16, 1977

[54] METHOD OF KILLING MICROORGANISMS IN THE INSIDE OF A CONTAINER UTILIZING A PLASMA INITIATED BY A FOCUSED LASER BEAM AND SUSTAINED BY AN ELECTROMAGNETIC FIELD

[75] Inventor: Lowell G. Tensmeyer, Indianapolis, Ind.

[73] Assignee: Eli Lilly and Company, Indianapolis, Ind.

[21] Appl. No.: 699,010

[22] Filed: June 21, 1976

[51] Int. Cl.$^2$ ............................................... A61L 1/00
[52] U.S. Cl. ................................. 21/54 R; 21/102 R; 219/121 LM
[58] Field of Search .......................... 21/54 R, 102 R; 204/DIG. 11; 331/DIG. 1; 219/121 L, 121 LM, 121 P; 426/236, 320

[56] References Cited

U.S. PATENT DOCUMENTS

| 3,383,163 | 5/1968 | Menashi | 21/54 R |
|---|---|---|---|
| 3,701,628 | 10/1972 | Ashman et al. | 21/54 R |
| 3,817,703 | 6/1974 | Atwood | 21/54 R X |
| 3,851,436 | 12/1974 | Fraser et al. | 21/54 R X |
| 3,876,373 | 4/1975 | Glyptis | 21/54 R |
| 3,880,586 | 4/1975 | Murayama et al. | 21/54 R X |
| 3,941,670 | 3/1976 | Pratt | 21/54 R X |
| 3,948,601 | 4/1976 | Fraser et al. | 21/54 R |
| 3,955,921 | 5/1976 | Tensmeyer | 21/54 R |

OTHER PUBLICATIONS

Meyerand; "Laser Plasma Production–...Research"; AIAA Journal, vol. 5 (10); pp. 1730–1737; (1967).

*Primary Examiner*—Barry S. Richman
*Attorney, Agent, or Firm*—Ralph W. Ernsberger; Everet F. Smith

[57] ABSTRACT

Method of killing microorganisms in the inside of a container which comprises directing an electromagnetic field into such container, inducing a plasma therein by focusing a single-pulsed, high-power laser beam into said field and exposing the inside of such container to said plasma for from about 1.0 millisecond to about 1.0 second by sustaining said plasma with said electromagnetic field.

17 Claims, No Drawings

METHOD OF KILLING MICROORGANISMS IN THE INSIDE OF A CONTAINER UTILIZING A PLASMA INITIATED BY A FOCUSED LASER BEAM AND SUSTAINED BY AN ELECTROMAGNETIC FIELD

BACKGROUND OF THE INVENTION

1. Field of the Invention

This invention relates to a method of killing microorganisms in the inside of a container. More particularly, this invention relates to a method in which the inside of such container is exposed to a plasma induced by focusing a high-power laser beam in an electromagnetic field.

2. Prior Art

Killing of microorganisms, which when carried to totality constitutes sterilization, in containers into which are filled such substances as parenteral and other medications, foods, beverages, dairy products, and the like, has been practised for decades for the purpose of preventing the transmission of disease. Many methods have been devised to accomplish this purpose. Heat, both dry and wet, has been a popular method of killing microorganisms in the food, beverage and pharmaceutical arts for a long time. The use of chemicals such as formaldehyde, phenol, ethanol, ethylene oxide, and the like for killing microorganisms has found many useful applications. More recently irradiation, such as beta, gamma, and ultraviolet rays have been employed in specialized applications for killing microorganisms.

In 1968, U.S. Pat. No. 3,383,163 described a method of sterilizing the surface of a material which does not conduct electricity comprising contacting such surface with a gaseous plasma at an extremely high temperature. In this method a corona discharge was utilized to generate a plasma inside a container. The corona discharge was achieved by introducing a grounded electrode into the container, surrounding the container with a coil and pulsing from about 5000 to about 7000 volts and above into the coil. Exposure of the surface to a plasma for a very brief period of time, normally not longer than one-tenth of a second, is described.

In the interval since U.S. Pat. No. 3,383,163 was issued, many attempts have been made to develop the plasma sterilization process into an economically feasible method because of the inherent advantage of killing and the microorganisms in the inside of a container just prior to filling. However, the mechanical problems associated with introducing a grounded electrode into a container and simultaneously surrounding the container with a high voltage coil have been found to be of such a magnitude as to defeat exploitation of the invention. Moreover, the volume of plasma generated by the corona discharge is dependent on the style and shielding of the electrode tip, the winding of the high voltage coil and the potential difference between said electrode and said coil at the moment of the pulsed discharge, and such requirements have presented problems in the location of the electrode and coil so as to fill the container with plasma. Furthermore, the voltage required to initiate the corona discharge is substantial and requires specialized electrical circuitry.

U.S. Pat. No. 3,955,921 describes a novel method of killing microorganisms inside of a container by repeatedly sparking an ultra-short-pulsed laser beam in the inside of the container. Each spark resulted in an ultra-short-lived plasma. This method has the advantage of inducing the microorganism killing plasmas within the container without the need for the mechanical introduction of an element into the containers. Moreover, microorganisms were killed in the inside of the container without contacting the inside surfaces of the container with the plasma. However, the need for a succession of independently generated plasmas extended the time which each container had to be in position for the laser beam to be focused thereinto.

Accordingly, it is an object of this invention to provide a method of killing microorganisms in the inside of a container with a continuous plasma that is induced by a single pulse of a focused high-power laser beam and is expanded and sustained inside such container for whatever interval is required to effect a complete killing of all microorganisms therein.

SUMMARY

It has now been discovered that a single pulse of a focused high-power laser beam in an electromagnetic field generated in the inside of a container immediately before the laser beam is pulsed therein will result in a plasma that can be sustained at will by maintaining sufficient energy in the electromagnetic field. The plasma is maintained for as long as it is needed to effect the desired degree of microorganism kill and is then stopped by extinguishing the electromagnetic field, or by moving the container out of the electromagnetic field. The duration of the plasma required for sterilization is a function of the power delivered to the plasma.

DESCRIPTION OF THE PREFERRED EMBODIMENTS

The novel method of this invention of killing microorganisms in the inside of a container comprises generating an electromagnetic field in the inside of such container and pulsing a focused, high-power laser beam in such field inducing a plasma that is expanded and sustained by the energy in the electromagnetic field. Said plasma is achieved by focusing said beam to a point of convergence (focal point) inside of said container, and at a sufficient distance from the inside surface of said container to avoid a contact of said surface by said plasma at the instant of the pulse.

The electromagnetic field on the inside of the container is achieved by positioning the container in an appropriate location where the electromagnetic field is concentrated or to which such field is guided or directed. Illustrative of such a positioning is the use of cavity at the end of a wave-guide tunnel in which there is an electromagnetic radiation-generating means; said cavity being tuned to concentrate the energy in the electromagnetic field at the locus of the container situated therein. Another illustration embraces the positioning of the container between the source of the electromagnetic radiation and a parabolic dish designed to reflect and concentrate the electromagnetic energy at the locus of the container. The mechanics of the dimension of the delivery means utilized to concentrate and direct the electromagnetic radiation are a function of the frequency of the generating means. Those skilled in the art will recognize this relationship.

Electromagnetic radiation generating means can theoretically be provided to yield oscillating frequencies from very low frequencies (VLF) up through radio frequencies (rf) to gamma rays, but for the purposes of this invention the frequencies generally fall within the range of from about $10^5$ to about $10^{16}$ hertz. Even so, from a practical consideration there are only a relatively small number of specific frequency bands in the electromagnetic radiation spectrum that have been allocated by the Federal Communications Commission (FCC) for industrial, scientific and medical use. Representative of these bands are: 13.36–14.00 megahertz (MHz), 27.23–27.28 MHz, 40.66–40.70 MHz, 0.915 gigahertz (GHz), 2.45 GHz and 22–22.125 GHz. The expressed limitations hereinabove described are FCC regulated limitations and do not otherwise constitute limitations attendant to the invention. Moreover, additional practical considerations involve the availability of electronic systems that limit the generation of electromagnetic fields to bands that are specific and narrow. No useful economic purpose is served by generating the electromagnetic fields at an infinite number of specific frequencies. Other electromagnetic energy bands useful in their invention are: 28.2 terahertz (THz), 282 THz and 431 THz. Should additional bands be allocated to such purposes as are consistent with this invention, such additional bands will be equally operative within the $10^5$ to $10^{16}$ spectrum and will only require the adaptation of the mechanics of the delivery means to the additional frequency or frequencies; a procedure which is known to those skilled in the art.

The electromagnetic radiation field is supplied with sufficient energy to expand and sustain the plasma once it has been initiated by the focused laser beam. For example, it was found that about 1.2 KW of energy output from a magnetron tube was needed to expand and sustain a laser beam-induced plasma in air in an electromagnetic radiation field having a frequency of 2.45 GHz.

The maintenance of a plasma in argon at atmospheric pressure by means of electromagnetic energy requires a minimum field intensity. It was found that these figures were approximately the following:

| Frequency | Field Intensity | Power Input to Generating Means |
|---|---|---|
| 2.45 GHz | 100 watts/cm$^2$ | 0.8 KW |
| 27 MHz | 275 watts/cm$^2$ | 2.2 KW |
| 5.2 MHz | 560 watts/cm$^2$ | 4.5 KW |

Additionally, there is a relationship between the energy in the electromagnetic field and the sterilizing capacity of the plasma. The greater the energy in the field, the greater the sterilizing capacity of the plasma and the shorter the exposure time required to effect sterilization. For example, it was found that at a frequency of 2.45 GHz it required about 1.2 second to achieve a one-decade, or 90%, kill of B. subtilis spores in a conventional 10 ml. ampoule when the power absorbed by the plasma was about 0.2 KW. The same kill rate ws achieved in 0.3 seconds when the power absorption was about 0.5 KW. Similar ampoules were sterilized in 0.9 seconds by a 0.5 KW plasma. It was calculated that with 1000 and 2000 watts, respectively, in the plasma, sterilization would be accomplished in 0.1 and 0.02 seconds, respectively. However, there is a mechanical and economic limit to the application of high energy to the electromagnetic field. Too much energy in the field will result in damage to the material with which the container is made by direct absorption of electromagnetic energy. Moreover, there is no economic benefit from the use of such energy that results in a rate of sterilization that is inconsistent with the need for rapid but not excessively rapid sterilization.

It is also to be noted that the lower the frequency the greater the energy needs to sustain the plasma. Illustratively, frequencies of 13.36–14.00 et. seq. MHz, and 0.915 HGz would require a greater energy input to sustain and/or expand the laser beam-induced plasma, and the 22–22.125 GHz frequency needs less energy input to accomplish the same phenomenon than the 2.45 GHz frequency.

In a preferred embodiment of this useful invention, a mechanical system comprising a wave-guide tunnel with an electromagnetic radiation generating means, such as a magnetron tube positioned therein and a cavity defined at one end thereof for the positioning therein of the container to be sterilized is constructed of an electrical conducting material, such as 12 gauge steel plate which is opaque to electromagnetic radiation at these frequencies, confines the field to the dimensions of the wave-guide tunnel and prevents the radiation energy from escaping into space. The cavity is tuned to the frequency of the electromagnetic field by means well known to those skilled in the art. It was found that a bi-modal cavity, at the least, was required for the efficient concentration of the electromagnetic radiation energy at the locus of the container positioned therein. At least two modes are required to accomodate the change in resonance as the plasma is ignited and expanded. A n-modal cavity will provide even greater efficiency.

The wave-guide tunnel is also tuned in volume to the frequency of the electromagnetic radiation. The lower the frequency the greater the cross-sectional area required. Such a guide is essential to concentrate and direct the electromagnetic radiation into the area in which the container to be sterilized is positioned. An internally located heat transfer means, such as a three part circulator with a water load, was required in the wave-guide tunnel to dissipate the heat of the unused reflected energy.

Inasmuch as the novel method of this invention contemplates a usefulness over a wide range of container sizes, from small vials employed for parenteral medications up to large food containers such as gallon jars, it can be seen that a single set of dimensions for a wave-guide tunnel and cavity are not appropriate as the physical size of the container will limit the dimension of such a tunnel and cavity. While a small container can be positioned in a cavity having a large volume, such would constitute an uneconomic arrangement inasmuch as the lower frequency radiations associated with large cross-sectional tunnels require a higher energy input to sustain the plasma for a sterilizing period. Consequently, the total installation should be considered in relation to the highest radiation frequency, requiring the lowest energy input, that is appropriate for the size of the container to be sterilized.

Many materials of which containers are made such as glass, plastics in general, ceramic ware and the like, are transparent to electromagnetic radiation; and for these it is only necessary that they be positioned in the electromagnetic field. The electromagnetic radiation will fill the container spontaneously as it is generated. Other container materials such as steel, aluminum, copper and other conducting metals, and the like, are opaque to electromagnetic radiation; and in such an event the cavity at the end of the wave-guide tunnel must be so designed that the container is actually a part of the mechanics of the cavity, and the container must have an opening therein which is transparent to electromagnetic radiation to permit such radiation to enter and fill the container. Those skilled in the art will understand such needs as being integral with the design of the cavity.

The electromagnetic field utilized in the preferred embodiment of the useful method of the instant invention can be either a pulsed or a CW field. When a 2.45 GHz magnetron tube was employed in the wave-guide tunnel the field was pulsed 120 times a second. Such a field is suitable for the propagation of a plasma and the sustaining thereof when sufficient energy is fed thereinto. Inasmuch as the pulse of the laser beam which initiates the plasma is measured in nanoseconds, which is described hereinafter, it is essential that the laser pulse shall be fired before the pulse of the electromagnetic field moves much past peak field strength; preferably the laser pulse occurs just before the electromagnetic field pulse reaches peak field strength. If the laser pulse is fired too early in the ascendancy of the energy in each individual pulse of the electromagnetic field, there will not be efficient coupling of the energy in the laser individual plasma and the electromagnetic field; and, consequently, the plasma will not be sustained. A similar phenomenon occurs when the laser is pulsed too far after the electromagnetic pulse has reached peak field strength. It is also to be noted that as the energy in each electromagnetic pulse is increased, the interval during which the laser can be pulsed to effect a coupling of the energies to sustain the plasma is increased.

When a CW electromagnetic field is used in the novel method of this invention the electrical circuitry provides for the ascendancy of properly phased following pulses to intersect with the descendency of a preceding pulse creating a continuous wave of energy, although such a CW field exhibits an undulating energy level. When the CW field is fed sufficient energy that at the point of intersection between following and preceding pulses a plasma sustaining intensity of energy is present, it is of no consequence when the laser is pulsed.

The focused, high-power laser beam, employed in the novel method of this invention to initiate the plasma, was achieved by Q-switching or mode-locking a laser beam, each pulse thereof having a duration of from about one-tenth to about 300 nanoseconds. The mechanics and methods of Q-switching and mode-locking laser beams to produce pulsed beams of short duration are old and well known to those skilled in the art, and constitute no part of the instant invention. In general, a high-power laser beam is one that contains megawatts of power.

The mechanics and methods of generating a plasma by focusing a high-power laser beam at a focal point where the cone of said beam converges are also well known to those skilled in the art. Optics appropriate to the wave length are employed in focusing a high-power laser beam. The focal point of the cone of the high-power laser beam must be sufficiently short to assure the generation of a spark on each pulse. Such focal point is a function of the energy in said beam; there being a direct relationship between the beam energy and the maximum focal point distance which unfailingly achieves a plasma with each pulse. The maximum focal length can be increased by increasing the energy in the beam.

The instant invention does not depend on the energy in the beam, but rather the generation of a plasma at the focal point. Any high-power laser beam which will form plasma at its focal point when such focal point is located within the inside of a container will effectively initiate a plasma in the inside of said container when said container is filled with an electromagnetic field. It will be understood that it is a function of the mechanics of an installation in which the inside of containers are sterilized to coordinate the positioning of the optics which are employed to focus the high-power laser beam with the beam energy which will produce a plasma at the focal point of said beam located inside of said containers.

A laser beam can be focused through a material that is optically clear and which does not appreciably distort the converging cone of the beam. So it is possible to accomplish the killing of microorganisms on the inside of a container in which there is no opening, or one in which the opening is insufficient for focusing a laser beam therethrough by focusing a laser beam through the material of which the container is made, if such material is also transparent to an electromagnetic field so that such a field is present in the inside of the container when the laser beam is focused therein. However, the greater number of the containers in which microorganisms will be killed by the useful method of this invention will be made of materials which do not meet the criteria noted above. Consequently, it is preferable that the containers, in which microorganisms will be killed by the novel process of the present invention, have an opening therein, and that the high-power laser beam be focused through such opening.

Consequently, the size of the opening in the container must be considered in designing a beam and the focusing thereof as a partial distortion of the converging sides of the cone of said focused beam by a contact with the material of which the container is made can corrupt said beam and interrupt the sparking thereof.

In the instant invention "plasma" defines a highly or essentially completely ionized body of gas which is composed of positively charge nuclei and negatively charged electrons, and exists at an extremely high temperature, perhaps approaching that of the sun. The life of the plasma of a focused, high-power laser beam is of exceptionally short duration, being in the neighborhood of from about 5 nanoseconds to about 5 microseconds longer than the laser pulse which initiates and sustains it.

While the exact mechanism by which the plasma initiated by a focused, high-power laser beam and expanded and sustained by electromagnetic radiation energy accomplishes the killing of microorganisms in the inside of a container in which said plasma is induced is not known, it is known that it is not necessary that the inside surfaces of said container be contacted by said plasma.

The plasma which is the result of the ionization of the gas inside said container by the focused, high-power laser beam can be formed from many ionizable gases. Air, comprised of nitrogen and oxygen, will form a plasma. Other ionizable diatomic gases, such as the halogens, will form plasmas, however, the preferred gases for plasma formation are monatomic gases such as argon, helium, xenon, neon, and the like. Irrespective of the gas utilized, the firing of a focused, high-power laser beam within the body of said gas induces a plasma which is expanded and/or sustained by the energy in the electromagnetic field.

In a preferred embodiment of the instant invention, a monatomic gas is introduced into the container, in which microorganisms are to be killed, prior to the generation of a plasma in said container. The monatomic gases are easier to ionize then oxygen or nitrogen; consequently, less energy is required to generate a plasma. An especially preferred embodiment constitutes the introduction of argon into the container prior to the generation of a plasma therein because such gas is plentiful and economic, and the residue thereof is limited to neutral argon.

Furthermore, plasmas can be formed from ionizable gases when the pressure within said container, wherein said focused, high-power laser plasma is generated, is other than atmospheric. The pressure can be either sub- or superatmospheric. And again, regardless of the pressure of the ionizable gas, the pulsing of a focused, high-power laser beam can be adjusted to initiate a plasma, which in turn is effective in killing microorganisms in the inside of a container, when such plasma is generated therein. Moreover, the electromagnetic field in the inside of said container is effective in expanding and sustaining the plasma regardless of the identity of the gas or the pressure in the container, with the energy levels varying with such condition. Such levels being well known to thos skilled in the art.

The key to the useful method of this invention lies in combining the pulsing of a focused, high-power laser beam in the inside of a container with the presence of an electromagnetic field within such container, said field having sufficient energy therein to sustain the plasma induced by the laser beam spark for a duration of from about 1.0 millisecond to about 1.0 second to effect a complete killing of the microorganisms in said container. The total elapsed duration of the plasma required to achieve the killing of microorganisms in the inside of a container wherein said plasma is initiated by a focused, high-power laser beam and sustained by an electromagnetic field varies with the energy absorbed in the plasma. The electrical properties of the material of which the container is constructed are of importance only with respect to the mechanical design of the apparatus which directs and concentrates the electromagnetic radiation energy in the container, as the plasma is generated by forces entirely within the confines of the container. It is preferred that the total accumulated exposure to the plasma be held to the minimum consistent with the total killing of the microorganisms in the inside of the container. Moreover, inasmuch as some aspects of the laser spark can be likened to a sonic boom, it is imperative that the focal point of the high-power laser beam be located at a sufficient distance from any point or part of the inside surface of said container to avoid the contacting of said inside surface by the plasma initiated by the laser beam pulse.

Typical containers in which the microorganisms present therein can be killed by plasmas initiated by pulsing a focused, high-power laser beam inside thereof, and sustaining such plasma by an electromagnetic field, are ampoules and vials used for parenteral and other medications, beverage bottles and cans such as those used for soft drinks, ber and ale, orange and lemon concentrates, and the like, milk bottles and cartons, baby food jars and cans and canned food containers, and the like.

This invention is further illustrated by the following example.

EXAMPLE 1

This experiment was run to determine the effect of a plasma generated on the inside of a container by pulsing a focused high-power laser beam in an electromagnetic radiation field on the bacterial count within said container.

Nine 10 ml. sterile vials having a 0.5 inch neck opening were each inoculated with about 125 spores of *Bacillus subtilis*. The *B. subtilis* was suspended in water. After inoculation, each vial was swirled to distribute the *B. subtilis* suspension on the inside surface thereof, and the vials were freeze dried. The dried inoculated vials were then closed with sterile rubber stoppers. For uninoculated sterile vials were also stoppered and utilized as controls.

A tuned delivery means comprising a cavity at the end of an appropriate wave-guide tunnel with a 2.45 GHz magnetron tube in position therein was equipped with a receptacle for the positioning of the vials and a focused high-power laser was located at an appropriate place so that a beam therefrom would be focused through the opening in the vial to converge at a point within the inside of the vial. Electrical circuitry was installed to fire the laser about 1.1 millisecond following the initiation of 120 Hz pulses from the nagnetron tube. A means for purging the vials with argon gas prior to the generation of the plasma was provided.

In turn each of the nine *B. subtilis* contaminated vials and the four sterile vials were treated as follows:

Two of the sterile vials were left unopened at the work area.

Two of the sterile vials were unstoppered, positioned in the dilivery means, purged with argon, restoppered and left at the work area.

Two of the contaminated vials were left unopened at the work area.

Two of the contaminated vials were unstoppered, placed in the delivery means, purged with argon, restoppered and left at the work area.

Three of the contaminated vials were unstoppered, placed in the delivery means, purged with argon, exposed to the electromagnetic field and an uncoupled pulse from the laser beam which did not yield a sustained plasma, restoppered and left at the work area.

Two of the contaminated vials were unstoppered, placed in the delivery means, purged with argon, exposed to a plasma initiated by a pulse from a focused high-power laser beam and sustained and expanded for about 1.0 second by a 2.45 gHz electromagnetic field providing a power absorption of about 0.2 KW, restoppered and left at the work area.

All 13 of the vials were submitted for microbiological testing with the results shown in Table 1 below.

Table 1

| Ampoule Treatment | Sterile Controls | | Contaminated Ampoules | | | |
|---|---|---|---|---|---|---|
| | Unopened | Unstoppered, Argon Swept, Restoppered | Unopened | Unstoppered, Argon Swept, Restoppered | Unstoppered, Argon Swept, Exposed to Microwave & Laser Spark, But Not Plasma, Restoppered | Unstoppered, Argon Swept, Exposed to Plasma, Restoppered |
| Final Condition (spores/ampoule) | Sterile | Sterile | 113 + 6 | 115 ± 50 | 22 ± 5 | Sterile |

Table 1-continued

| Ampoule Treatment | Sterile Controls | | Contaminated Ampoules | | | |
|---|---|---|---|---|---|---|
| | Unopened | Unstoppered, Argon Swept, Restoppered | Unopened | Unstoppered, Argon Swept, Restoppered | Unstoppered, Argon Swept, Exposed to Microwave & Laser Spark, But Not Plasma, Restoppered | Unstoppered, Argon Swept, Exposed to Plasma, Restoppered |
| Actual Microbiology Report | <3 <3 | <3 <3 | 119 107 | 65 165 | 20 29 17 | <3 |

The microbiology report "<3" is a reflection of the aliquoting process in which the vial is washed thoroughly, one-third of the wash is cultured, and the result is multiplied by 3. Thus, a completely sterile ampoule is reported "<3."

The data in Table 1 indicate the effectiveness of a plasma induced by a single pulsed high power laser beam and sustained by electromagnetic radiation energy in killing microorganisms in the inside of a container wherein such plasma is generated and sustained.

What is claimed is:

1. A method of killing microorganisms in the inside of a container comprising directing into the container an electromagnetic field having sufficient energy therein to sustain a plasma, focusing a high power laser beam at a focal point in the inside of the container, the focal point being at a sufficient distance from the inside surface of the container to avoid contacting the surface with the spark resulting from the convergence of the laser beam at the focal point thereof, pulsing the laser beam once and thereby initiating a plasma in the electromagnetic field, and sustaining the plasma for a sterilizing period with the energy in the electromagnetic field.

2. The method according to claim 1 wherein the electromagnetic field is characterized by radiation energy having a frequency of from about $10^5$ to about $10^{16}$ hertz.

3. The method according to claim 1 wherein the electromagnetic field is characterized by radiation energy having a frequency of from about 13.36 to about 14.00 megahertz.

4. The method according to claim 1 wherein the electromagnetic field is characterized by radiation energy having a frequency of from about 27.23 to about 27.28 megahertz.

5. The method according to claim 1 wherein the electromagnetic field is characterized by radiation energy having a frequency of from about 40.66 to about 40.70 megahertz.

6. The method according to claim 1 wherein the electromagnetic field is characterized by radiation energy having a frequency of about 0.915 gigahertz.

7. The method according to claim 1 wherein the electromagnetic field is characterized by radiation energy having a frequency of about 2.45 gigahertz.

8. The method according to claim 1 wherein the electromagnetic field is characterized by radiation energy having a frequency of about 28.2 terahertz.

9. The method according to claim 1 wherein the electromagnetic field is characterized by radiation energy having a frequency of about 282 terahertz.

10. The method according to claim 1 wherein the electromagnetic field is characterized by radiation energy having a frequency of about 431 terahertz.

11. The method according to claim 1 wherein the electromagnetic field is generated in a wave-guide tunnel tuned to the frequency of the radiation energy employed for expanding and sustaining the laser beam generated plasma, and directed into the container to be sterilized positioned inside of a cavity at the end of the wave-guide.

12. The method according to claim 1 wherein the plasma is sustained for a sterilizing period of from about 1.0 millisecond to about 1.0 second.

13. The method according to claim 1 wherein the electromagnetic field is characterized by radiation energy having a frequency of about 22–22.125 gigahertz.

14. The method of claim 13 wherein the electromagnetic field is a pulsed field generated 120 times per second.

15. The method of claim 13 wherein the electromagnetic field is a CW (continuous wave) field.

16. The method of killing microorganisms in the inside of a container having an opening therein comprising:
   a. positioning said container in a cavity at the end of a wave-guide tunnel tuned to cooperate with a microwave field wherein the frequency of the electromagnetic radiation energy is about 2.45 gigahertz;
   b. introducing a monatomic gas into said container through said opening;
   c. generating a microwave field having a frequency of 2.45 gigahertz and an electromagnetic radiation energy of about 0.5 kilowatts in said wave-guide tunnel, and directing said energy to said cavity wherein said container is positioned;
   d. directing a focused high-power laser beam through said opening to a focal point in the inside of said container, said focal point being at a sufficient distance from the inside surface of said container to avoid contacting said surface with the spark resulting from the convergence of said laser beam at said focal point thereof;
   e. initiating a plasma in said electromagnetic field by pulsing said laser beam once therein; and
   f. exposing the inside of said container to said plasma for from about 1.0 millisecond to about 1.0 second.

17. The method of killing microorganisms in the inside of a container having optically clear walls transparent to the passage of electromagnetic radiation energy comprising positioning said container in a cavity at the end of a wave-guide tunnel tuned to the frequency of said radiation energy, generating a field of electromagnetic radiation energy within said wave-guide tunnel and delivering said energy into said cavity, said field of electromagnetic energy having sufficient energy therein to sustain a plasma, directing a focused high-power laser beam to a focal point on the inside of said container and at a distance from the inside surface thereof which avoids contacting said surface with the spark resulting from the convergence of said beam at the focal point thereof, pulsing said laser beam once and thereby inducing the generation of a plasma on the inside of said container and sustaining said plasma with said field of electromagnetic energy for a sterilizing period of from about 1.0 millisecond to about 1.0 second.

* * * * *